United States Patent
Wiedner

[19]

[11] Patent Number: 5,805,258
[45] Date of Patent: Sep. 8, 1998

[54] ONE-PIECE INDUSTRIAL SAFETY GLASSES HAVING FOREHEAD CUSHIONING PORTION

[75] Inventor: Klaus Wiedner, Fürth, Germany

[73] Assignee: Uvex Arbeitsschutz GmbH, Fürth, Germany

[21] Appl. No.: 832,059

[22] Filed: Apr. 2, 1997

[30] Foreign Application Priority Data

Jul. 4, 1996 [DE] Germany .................. 296 11 652 U

[51] Int. Cl.⁶ ............................................. G02C 1/02
[52] U.S. Cl. ................................... 351/110; 351/41
[58] Field of Search .................... 351/110, 43, 41, 351/62, 158

[56] References Cited

U.S. PATENT DOCUMENTS 5,495,303  2/1996  Kolentsi .

FOREIGN PATENT DOCUMENTS

94/03831  2/1994  WIPO .

Primary Examiner—Hung X. Dang
Attorney, Agent, or Firm—Browdy and Neimark

[57] ABSTRACT

In industrial safety glasses comprising a one-piece plastics sight piece and a top of comparatively soft plastics on the forehead side which can be fixed to the sight piece and has a groove open toward the sight piece, it is provided, with a view to simple producibility, reliable arresting of the top and reliable protection of the user's eyes, that the top is injection-molded on the sight piece.

12 Claims, 2 Drawing Sheets

ONE-PIECE INDUSTRIAL SAFETY GLASSES HAVING FOREHEAD CUSHIONING PORTION

BACKGROUND OF THE INVENTION

1. Field of the Invention

The invention relates to industrial safety glasses comprising a one-piece plastics sight piece and a top on the forehead side of comparatively soft plastics which is fixed to the sight piece and has a groove open toward the sight piece.

2. Background Art

Known industrial safety glasses of the generic type have an upper horizontal section extending toward a user's forehead and approximately conforming to the contour of the forehead. However, the inner edge of such a section can conform to the individual shape of a user's forehead only approximately so that clearances of different size remain between the glasses and the forehead, allowing splashes and particles, in particular dust, to enter.

Attempts have been made to attain greater individualization by slip-on elements of rigid plastics being provided that extend over part of the upper side. This means a certain improvement, but does not help achieve a really flush covering of the upper side needed for dustproofing.

Protective glasses of the generic type are known from WO 94/03831, in which the top consists of foamed material, the top being fixed by gluing and having a slit for it to be slipped on and held in place mechanically for instance by ribs. Comparable strips of foamed material are also known from U.S. Pat. No. 5,495,303.

SUMMARY OF THE INVENTION

It is the object of the invention to embody protective glasses of the type mentioned at the outset in such a way that while offering high convenience of wearing, the glasses reliably protect the user's eyes against the penetration of dust, drops or the like, it being desirable that simple manufacture and reliable fixing of the top be ensured.

According to the invention, this object is attained by the top being injection-molded on the sight piece. The latter preferably consists of TPE or TPU, i.e. thermoplastic elastomer or thermoplastic polyurethane. These are plastics which combine well with the sight-piece material or the coating of the sight-piece material.

The top on the forehead side may have a front frame element comprising a groove open toward the sight piece, the actual top extending plane from the frame element toward the user's forehead.

Thus it is possible to injection-mold the frame piece around the edge of the sight piece and possibly also around the upper and lateral pieces joined on. The actual top of the upper side is comparatively thin, having for instance a thickness of approximately 1 mm. It consists of solid plastic material, i.e. not of foamed material, thereby ensuring that nothing can get into the user's eyes from the upper side. On the other hand the comparatively low thickness gives such a softness that good adapting to the configuration of the user's forehead is attainable. The smooth surface of the plastic material provides for good cleaning of the glasses. In this regard, the tops of foamed material conventionally used have considerable drawbacks. On the other hand, the top according to the invention can be made so thin that the required softness is obtained in spite of the use of a solid plastic material.

In keeping with another embodiment of the invention it can be provided that a preferably arc-shaped arresting section extending upward is molded on the inner edge of the piece that is joined to the sight piece and extends backward, this arresting section ensuring a good connection between the sight-piece material and the plastic material applied by injection-molding. To the same end, the upper and lateral pieces joined on may have openings, into which the plastic material penetrates during the application of the plastic material by injection-molding.

Favorably, the sight-piece tops are produced by two-component injection-molding.

In a preferred embodiment it is provided that a nose saddle and/or protector against scratching of the sight piece are applied to the nose portion of the sight piece by injection-molding; they can be formed in one piece with the top according to the invention and produced together with the latter in a single injection-molding job.

As a result of the top according to the invention which bears particularly tightly against the user's forehead, it is of special importance that the sight piece has an anti-fogging layer. In this regard, provision is made for the anti-fogging layer on the inside of the sight piece to comprise a combination of a hydrophilic polyurethane component, which has a water-absorbing effect, and a surface-active tenside, which prevents drop formation and causes the formation of a water film. The layer is produced in a one-pot process, the polyurethane component as well as the tenside being correspondingly deposited in one operation as a single layer.

Details of the invention will become apparent from the ensuing description of a preferred exemplary embodiment, taken in conjunction with the drawing.

DESCRIPTION OF THE PREFERRED EMBODIMENT

Figure 1:
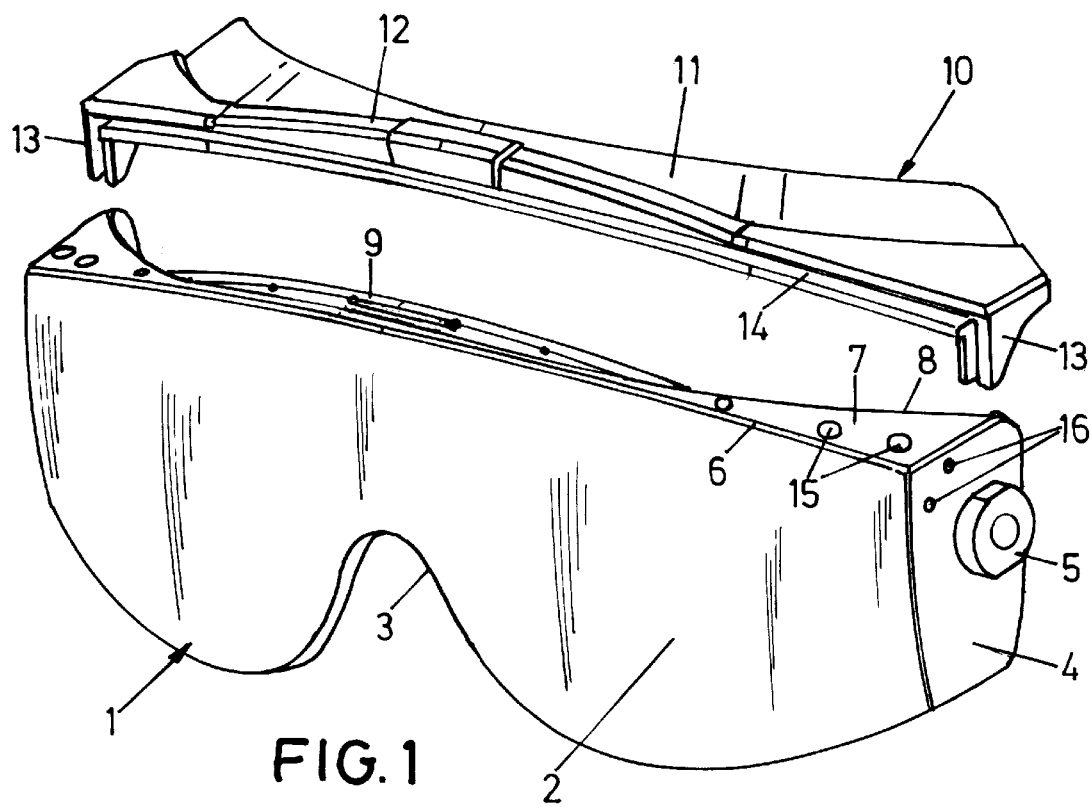
FIG. 1 is a perspective view, in the nature of an exploded view, of a sight piece of a pair of industrial safety glasses according to the invention with an associated top on the forehead side seen from the front.

A pair of industrial safety glasses seen in the drawing comprises a onepiece plastics sight piece 1 with a front sight field 2 and a nose-piece portion 3, joined-on pieces 4 extending laterally backwards from the sight field 2 and having bearing studs 5 applied by injection-molding for side pieces (not shown). A piece joined on 7 that is horizontal in the condition of use extends along the upper edge 6 of the sight field 2, its inner edge 8 conforming about to the curvature of the user's forehead. Along the middle portion of the upper edge 6, an arc-shaped, joined-on arresting piece 9 extends vertically upwards from the edge 6.

A top 10 is injection-molded, forming a single piece of comparatively soft plastic material and comprising a horizontal plane element 11 and a frame element 12 running along the latter's front edge and having sections 13 that overlap the lateral pieces 4 joined on.

The top 10 has a groove 14. However, when injection-molded, the top 10 is not realized in the isolated form seen in FIG. 1, because the comparatively soft plastic material constituting the top 10 is injection-molded around the sight piece in the mold. For a tight union to be obtained between this soft plastic material and the sight-piece material, the joined-on pieces 7 and 4 are provided with openings 15 and 16 so that the plastic material of the top 10 may penetrate them, the top thus being fixed by positive fit. Consequently, a finished product is created as illustrated in FIG. 2.

Figure 2:
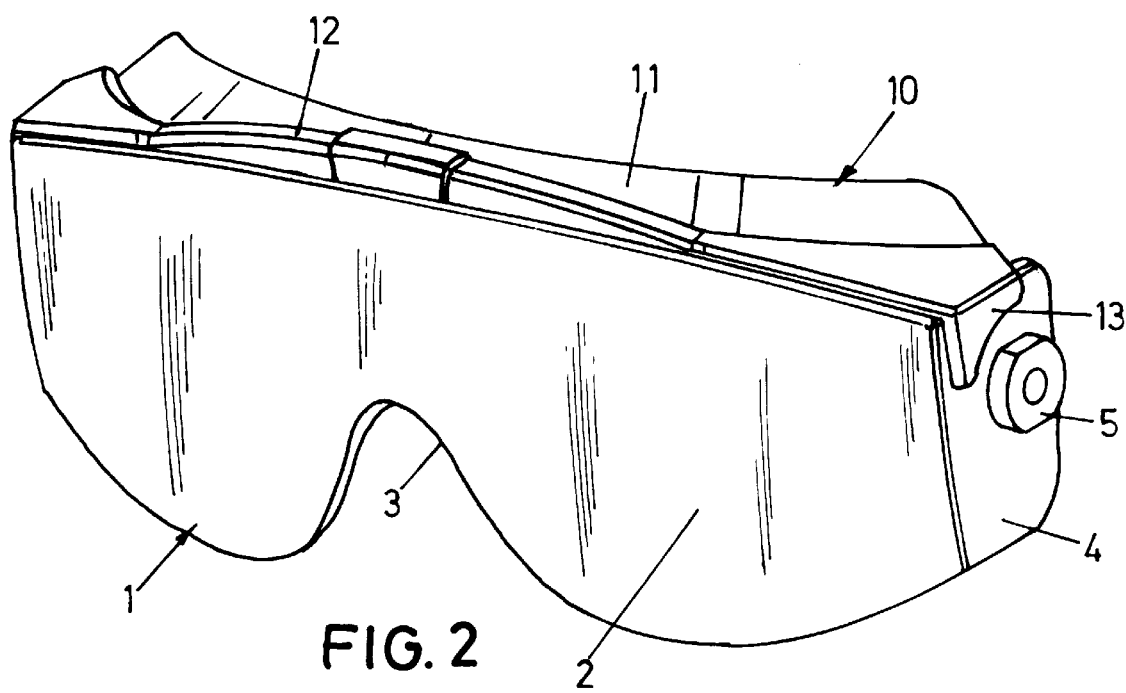
FIG. 2 is an illustration of the glasses or of the sight piece of FIG. 1 in the condition of use.
Figure 3:
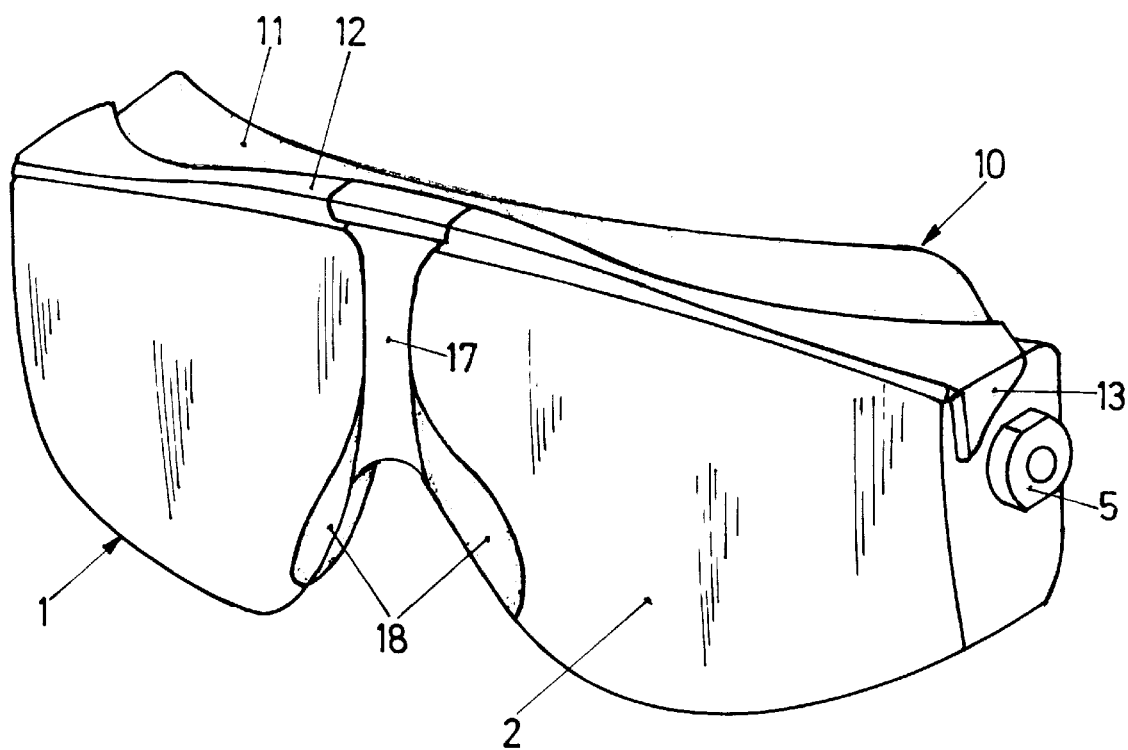
FIG. 3 is an illustration corresponding to FIG. 2 of a modified embodiment.

According to FIG. 3, a protector against scratching 17 is injection-molded on the frame 12 of the top 10 of the FIG. 1 device, virtually extending parallel to the nose portion on the outside of the sight piece 1 and running into nose pieces 18.

What is claimed is:

1. Industrial safety glasses comprising a one-piece plastic sight piece and a top portion of comparatively soft plastic on the forehead side, the sight piece having a rearwardly facing upper edge, and the top portion having a forwardly facing groove overlapping said rearwardly facing upper edge of the sight piece, the top portion being injection-molded onto the sight piece so as to form a unitary construction.

2. Industrial safety glasses according to claim 1, wherein the top portion comprises a front frame part with said forwardly facing groove and a second part extending plane from the frame part rearwardly toward the user's forehead.

3. Industrial safety glasses according to claim 2, wherein the top portion on the forehead side is made of thermoplastic elastomer or thermoplastic polyurethane.

4. Industrial safety glasses according to claim 2, wherein said sight piece comprises a front portion and side pieces extending rearwardly from sides of said front portion, and the front frame part of said top portion is injection-molded around parts of said side pieces.

5. Industrial safety glasses according to claim 4, wherein said comparatively soft plastic of said top portion extends through openings in said sides of said sight piece.

6. Industrial safety glasses according to claim 2, wherein said sight piece comprises a front portion and a generally planar upper wall carrying said rearwardly facing upper edge, and the front frame part of said top portion is injection-molded around parts of said generally planar upper wall.

7. Industrial safety glasses according to claim 6, wherein said upper wall of said sight piece has an upwardly extending and generally arc-shaped arresting section injection-molded adjacent said rearwardly facing upper edge.

8. Industrial safety glasses according to claim 6, wherein said comparatively soft plastic of said top portion extends through openings in said upper wall of said sight piece.

9. Industrial safety glasses according to claim 2, wherein said sight piece comprises a front portion, side pieces extending rearwardly from sides of said front portion, and a generally planar upper wall carrying said rearwardly facing upper edge, and wherein said front frame part of said top portion is injection-molded around parts of said side pieces and at least parts of said upper wall.

10. Industrial safety glasses according to claim 9, wherein said upper wall of said sight piece has an upwardly extending and generally arc-shaped arresting section injection-molded adjacent said rearwardly facing upper edge.

11. Industrial safety glasses according to claim 1, further comprising at least one of a nose saddle and a protector against scratching of the sight piece unitarily injection-molded and one-piece with said sight piece at a nose portion thereof.

12. Industrial safety glasses according to claim 1 further comprising an anti-fogging layer on the inside of said sight piece, said anti-fogging layer comprising a combination of a hydrophilic polyurethane component having a water-absorbing effect and a surface-active tenside which prevents drop formation and causes the formation of a water film.

* * * * *